United States Patent [19]
Dotan

[11] Patent Number: 6,139,553
[45] Date of Patent: Oct. 31, 2000

[54] FACIAL TREATMENT IMPLEMENT AND METHOD

[76] Inventor: Simon Dotan, 47 Havradin Str., 42651 Natania, Israel

[21] Appl. No.: 08/934,738

[22] Filed: Sep. 22, 1997

[51] Int. Cl.[7] .................................................. A61B 17/50
[52] U.S. Cl. ............................ 606/131; 604/303; 601/70
[58] Field of Search .................................. 601/46, 67, 69, 601/72, 136–142, 23, 27, 30–32, 60, 65, 70, 71, 80, 81, 112; 606/131, 201, 204.15; 604/303; D28/7; 132/320, 317

[56] References Cited

U.S. PATENT DOCUMENTS

| | | |
|---|---|---|
| 1,919,571 | 7/1933 | Pinkston ................................. 601/136 |
| 2,809,631 | 10/1957 | Smith . |
| 3,169,536 | 2/1965 | Caracciolo . |
| 3,194,231 | 7/1965 | Caracciolo . |
| 3,991,751 | 11/1976 | O'rourke ................................... 601/72 |
| 4,291,685 | 9/1981 | Taelman . |
| 4,378,804 | 4/1983 | Cortese ................................... 606/131 |
| 4,655,232 | 4/1987 | Ficke . |
| 5,044,356 | 9/1991 | Fishman . |
| 5,140,979 | 8/1992 | Nakagawa . |
| 5,187,827 | 2/1993 | Wei ......................................... 601/138 |
| 5,395,380 | 3/1995 | Berkovich . |
| 5,587,396 | 12/1996 | Smith ..................................... 514/557 |
| 5,720,949 | 2/1998 | Davis ................................... 424/78.03 |
| 5,725,483 | 3/1998 | Podolsky ................................... 601/17 |
| 5,797,859 | 8/1998 | Prehodka ................................ 601/113 |
| 5,827,884 | 10/1998 | Obagi et al. ............................ 514/557 |
| 5,922,359 | 7/1999 | Youssefyeh ............................ 424/570 |

*Primary Examiner*—Glenn K. Dawson

[57] ABSTRACT

An implement for and a method of, facial treatment are described in which a facial preparation containing an abrasive is applied to the face, and a facial treatment head is pressed against the facial preparation and is vibrated to work the facial preparation into the skin of the subject's face. Preferably, the facial treatment head includes a convexly-curved surface, but may also be one including a rotary disk which is rotated and vibrated while pressed into contact with the facial preparation on the subject's face. The facial preparation is preferably a mud mixture; preferably, this treatment is followed by another one utilizing a facial preparation containing a moisturizer which is also worked into the skin in a similar manner as the mud treatment.

13 Claims, 2 Drawing Sheets

A

B

FACIAL TREATMENT IMPLEMENT AND METHOD

FIELD AND BACKGROUND OF THE INVENTION

The present invention relates to a facial treatment implement, and also to a method of facial treatment.

Attaining a fresh-appearing, youthful-looking, wrinkle-free facial skin has been a goal sought throughout recorded history, and many cosmetic treatments, as well as surgical procedures, have been provided in an attempt to attain such a goal.

An object of the present invention is to provide a facial treatment implement which can be used for improving the appearance of the facial skin. Another object of the present invention is to provide a facial treatment method for improving the appearance of the facial skin.

SUMMARY OF THE PRESENT INVENTION

According to one aspect of the present invention, there is provided a facial treatment implement, comprising: a portable housing manually graspable by a user; a rotary motor within the housing and having a rotary drive shaft; an eccentric member coupled to the rotary drive shaft to be rotated thereby; a first facial treatment head removably attachable to said rotary drive shaft at one end of said portable housing so as to be rotated by said drive shaft and also to be vibrated by said eccentric member; and a second facial treatment head removably attachable to the housing and including a surface for engaging the skin of the user; the second facial treatment head being uncoupled from the rotary drive shaft so as not to be rotated thereby, but being vibrated by the eccentric member when the facial treatment head is attached to the housing and the rotary motor is energized.

According to further features in the described preferred embodiment, the first facial treatment head includes a disk, and the second facial treatment head includes a convexly-curved surface, to be pressed against the user's skin.

According to another aspect of the present invention, there is provided a facial treatment implement, comprising: a portable housing manually graspable by a user; a rotary motor within the housing and having a rotary drive shaft; an eccentric member coupled to the rotary drive shaft to be rotated thereby; and a facial treatment head attachable to the housing and including a disk having a surface to be pressed into contact with a facial preparation on a user's face to perform a facial treatment thereof, the disk being coupled to the rotary drive shaft to be rotated thereby, and to be vibrated by the eccentric member, when the facial treatment head is attached to the housing and the rotary motor is energized.

According to a still further aspect of the present invention, there is provided a method of facial treatment, such method comprising: applying to a subject's face a facial preparation containing an abrasive; pressing a facial treatment head against the facial preparation on the subject's face and vibrating the head to work the facial preparation into the skin of the subject's face; and removing the facial preparation from the subject's face.

According to further features in the described preferred embodiment of the method, first used is a facial treatment head including a rotary disk which is rotated and vibrated while pressed into contact with the facial preparation of the subject's face, and then a facial treatment head is applied including a convexly-curved surface which is vibrated, but not rotated, while pressed in the contact with the facial preparation on the subject's face. The rotary disk head is preferably used with respect to the relatively flat or planar surfaces of the face, and the head including the convexly-curved surface is used with respect to the more sharply curved surfaces, such as around the nose and eye sockets, of the subject's face. The facial treatment head further includes a shield enclosing the disk and projecting past the surface thereof to be pressed into contact with the facial preparation on the user's face.

Such a facial treatment produces a "scrubbing" or "peeling" effect on the user's face. Preferably, this is followed by applying, after that facial preparation has been removed, a second facial preparation containing a moisturizer, which second preparation is also worked into the skin of the subject's face by a vibrating, and/or rotating head in the manner described above with respect to the first facial preparation.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
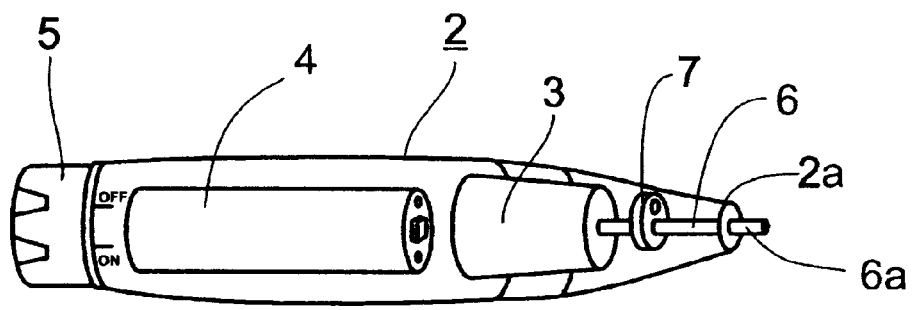
FIG. 1 is an exploded view illustrating the main components of one form of facial-treatment implement constructed in accordance with the present invention, including two types of facial treatment heads selectively attachable to the implement.
Figure 1:
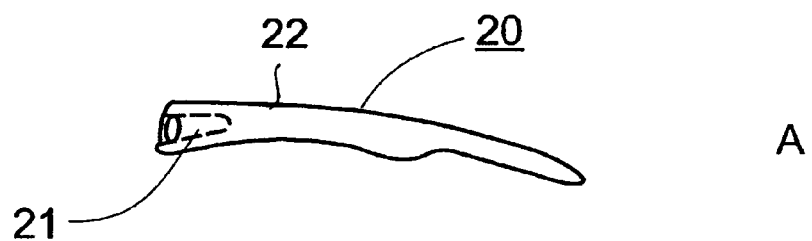
Figure 1:
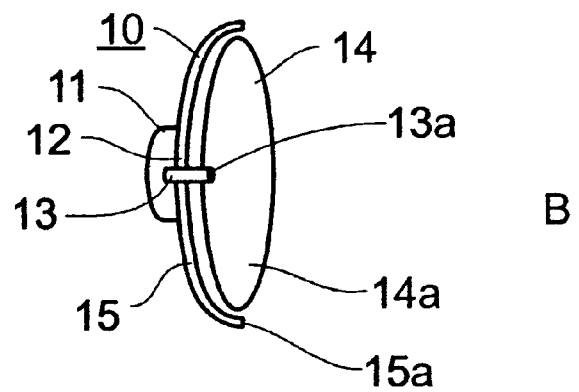

The facial treatment device illustrated in the drawings comprises a portable housing 2 manually graspable by the user, the housing enclosing a rotary motor 3 energized by batteries 4 under the control of a manual switch 5. Motor 3 includes a rotary drive shaft 6 having one end 6a projecting through housing end 2a. An eccentric member 7 disposed within housing 2 is coupled to the rotary drive shaft 6 so as to be rotated upon the energization of motor 3, and thereby to impart vibrations to the housing 2.

Figure 2:
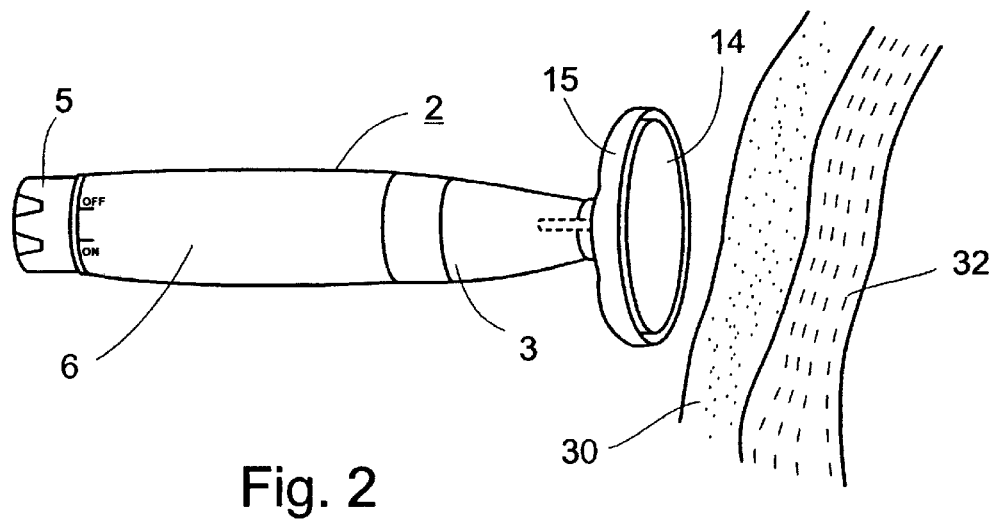
FIG. 2 illustrates the implement of FIG. 1 with one of the facial treatment heads attached.
Figure 3:
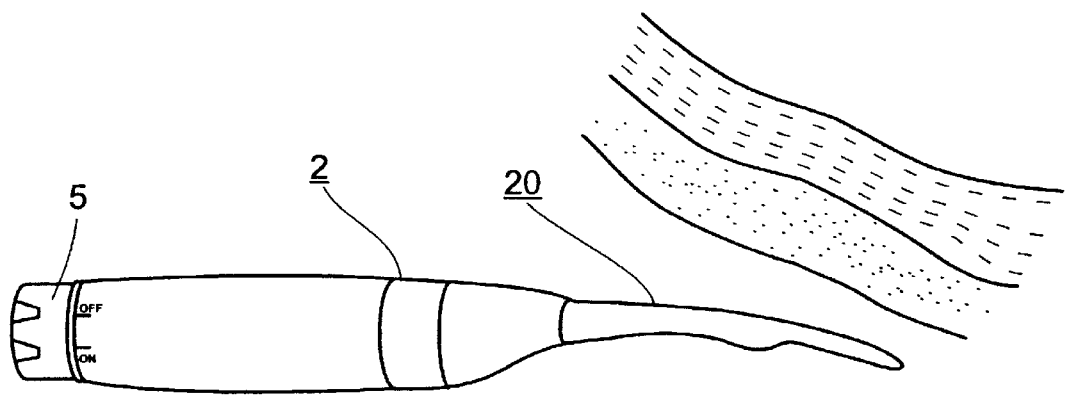
FIG. 3 illustrates the implement of FIG. 1 with the other faicial treatment head attached.

FIG. 1 illustrates two facial treatment heads, generally designated 10 and 20, respectively, to be selectively attached to end 2a of housing 2, as shown in FIGS. 2 and 3, respectively.

Facial treatment head 10 includes a collar 11 removably attachable, e.g. by a friction-fit, to end 2a of the housing 2, and a shaft coupling member 12 rotatably mounted with respect to collar 11. Coupling member 12 is formed with a socket 13 for receiving end 6a of the rotary drive shaft 6 so that the coupling member 12 is rotated with respect to collar 11 by the motor drive shaft 6.

Coupling member 12 is connected to a disk 14. Collar 11 is connected to a shield 15 enclosing disk 14 except for the outer face 14a of the disk.

As shown particularly in FIG. 1, the outer open end 15a of shield 15 projects past the plane of disk 14, such that the outer end of the shield may be pressed firmly into contact with the facial preparation on the face of the person receiving the facial treatment while the disk 14 is only in light contact with the facial preparation, as will be described more particularly below. The shield thus catches any of the facial preparation thrown out by the disk during the facial treatment.

FIG. 2 illustrates the implement having the facial treatment head 10 attached, i.e., with the collar 11 received with a friction fit on the end 2a of the housing, and with the rotary drive shaft 6a received within socket 13 of the rotary coupling member 12. Thus, when motor 3 is energized by moving the electrical switch 5 to its "on" position, disk 14 is rotated with respect to shield 15 and housing 2. Disk 14 is also vibrated (as well as rotated) since the eccentric member 7 coupled to the rotary drive shaft 6 produces vibrations in housing 2 and thereby in the facial treatment head 10 fixed by collar 11 to the housing.

The second facial treatment head 20, when attached to the implement housing 2, is not rotated by motor 3, but is merely vibrated by the eccentric member 7 coupled to the motor drive shaft 6. For this purpose, facial treatment head 20 is formed with a socket 21 which is received, e.g. by a friction fit, over the end 2a of housing 2. Socket 21 is dimensioned so as to be spaced from end 6a of the rotary drive shaft so as not to be rotated by that shaft.

Facial treatment head 20 is formed with an outer surface 22 of convex configuration. Surface 22 may be, for example, of a spoon-configuration. It is pressed against the facial preparation on the face of the user receiving the facial treatment particularly at the more sharply curved surfaces of the user's face, e.g., at the nose and eye regions.

The implement illustrated in the drawings may be used in the facial treatment of a person in the following manner:

As shown in FIG. 2, a facial preparation 30 is first applied to on the skin 32 of the person to be treated. The disk-type treatment head 10 is first used by attaching it to the end 2a of housing 2, with the projecting end 6a of the rotary shaft 6 received within socket 13 of the head coupling member 12. Head 10 is pressed against the facial preparation 30 on skin 32 with the projecting outer end 15a of shield 15 pressed firmly into contact with the skin, and with the surface 14a of the disk in light contact with the facial preparation 30 on the skin 32. Motor 3 is then energized, whereupon disk 14 is rotated, and also vibrated by eccentric member 7, to work the facial preparation against the skin 32, while the projecting end 15a of shield 15 prevents the facial preparation from splattering externally of the head.

The implement is slowly moved across all the relatively planar surfaces of the face while the rotation and vibration of disk 14 work the facial preparation into the user's skin.

After the implement has thus been applied to all the relatively planar surfaces on the face of the person receiving the treatment, head 10 is removed and head 20 is attached to end 2a of the housing 2. Head 20 is not rotated, but is merely vibrated by eccentric member 7. The outer convex surface 22 of head 20 permits the head to work the facial preparation into the more sharply curved surfaces of the person's skin, such as in the nose and eye regions.

After substantially the complete surface of the face has been so treated, first by head 10 and then by head 20, the facial preparation is then removed form the user's skin in any suitable manner.

The above-described implement and facial treatment method are useful with respect to various types of facial preparations. Following is one commercially known mud-mixture facial preparation which includes abrasive particles, and which thus produces a "scrubbing" or "peeling" effect;

Dead Sea mud, Locopheryl acetate (vitamin E), kaolin, witch hazel extract, polyethylene particles (constituting the, or part of the, abrasive particles), disodium EDTA, magnesium aluminium silicate, imidasolidinyl urea, hydroxyethylcelullose, propylene glycol, cetearyl alcohol, glycerylstearate, PEG-40-stearate, sorbilan tristearate, dibulyl adipate, methylparaben and ethylparaben and propylparaben and butylparaben and phenoxycthanol, fragrance, deionized water.

The above-described mud-mixture preparation is applied and partially dried, and then worked into the skin, first by the rotary-vibratory head 10, and then by the vibratory head 20. After it has been removed from the skin, a second facial preparation is applied containing a moisturizer. The moisturizer-type preparation is applied in the same manner, by the use of the two heads 10, 20, as the abrasive-type preparation and is then removed.

Following is an example of a commercially available moisturizer-type of facial preparation that can be used:

deionized water (aqua), octyloctanoate, cetearylisononanoate, octyl methoxycinnamate, glyceryl stearate, cetearyl alcohol, PEG-40-stearate, saccharide isomerate, aloe babadensis gel (aloe vera), glycerin, sorbitan tristearate, dead sea salt, magnesium aluminium silicate, panthenol, tocopheryl acetate, tocopherol, xanthan gum, methylparaben and ethylparaben and propylparaben and butylparaben and phenoxyethanol, disodium EDTA, fragrance.

While the invention has been described with respect to one preferred embodiment, including two examples of facial preparations that could be used, it will be appreciated that these are set forth merely for purposes of example, and that many other variations, modifications and applications of the invention may be made.

What is claimed is:

1. A facial treatment implement, comprising:

a portable housing manually graspable by a user;

a rotary motor within said housing and having a rotary drive shaft;

an eccentric member coupled to said rotary drive shaft to be rotated thereby;

a first facial treatment head removably attachable to said rotary drive shaft at one end of said portable housing so as to be rotated by said drive shaft and also to be vibrated by said eccentric member:

and a second facial treatment head removably attachable to said housing and including a surface for engaging the skin of the user;

said second facial treatment head being uncoupled from the rotary drive shaft so as not to be rotated thereby, but being vibrated by said eccentric member when the second facial treatment head is attached to the housing and the rotary motor is energized.

2. The implement according to claim 1, wherein said surface of said second facial treatment head is convexly curved.

3. The implement according to claim 2, wherein said first facial treatment head includes a disk having a surface to be pressed into contact with a facial preparation on a user's face.

4. The implement according to claim 3, wherein said first facial treatment head further includes a shield enclosing said disk and projecting the of said disk past the surface of said disk to be pressed into contact with the user's face to be treated.

5. The implement according to claim 4, wherein said shield is uncoupled from said rotary drive shaft and from said disk such that the shield does not rotate with the disk.

6. The implement according to claim 5, wherein said shield includes an outer end projecting past the disk enabling the shield to be pressed firmly into contact with the subject's skin, while the disk is in only light contact with the facial preparation on the subject's skin.

7. The implement according to claim 1, wherein said portable housing further includes a battery power supply, and an electrical switch for controlling the energization of said rotary motor.

8. A facial treatment implement, comprising:

a portable housing manually graspable by a user;

a rotary motor within said housing and having a rotary drive shaft;

an eccentric member coupled to said rotary drive shaft to be rotated thereby;

and a facial treatment head attachable to said housing and including a disk having a surface to be pressed into contact with a facial preparation on a user's face, said disk being coupled to said rotary drive shaft to be rotated thereby, and to be vibrated by said eccentric member, when the facial treatment head is attached to the housing and the rotary motor is energized;

said facial treatment head further including a shield enclosing said disk and projecting past said surface to be pressed into contact with the facial preparation on the user's face.

9. The implement according to claim 8, wherein said shield is uncoupled from said rotary drive shaft and from said disk such that the shield does not rotate with the disk.

10. The implement according to claim 9, wherein said shield includes an outer end projecting past the disk enabling the shield to be pressed firmly into contact with the subject's skin, while the disk is in only light contact with the facial preparation on the subject's skin.

11. The implement according to claim 7, wherein said facial treatment head is removably attachable to said portable housing.

12. The implement according to claim 11, wherein the implement includes a second facial treatment head removably attachable to said housing in place of the first-mentioned facial treatment head; said second facial treatment head being attachable to the housing so as to be vibrated by said eccentric member but not to be rotated by the rotary drive shaft of the rotary motor.

13. The implement according to claim 12, wherein said second facial treatment head includes a convexly-curved surface for enaging the facial preparation on the user's skin.

* * * * *